United States Patent [19]

Fukuoka et al.

[11] Patent Number: 4,587,056

[45] Date of Patent: May 6, 1986

[54] PROCESS FOR PRODUCING AN ALIPHATIC ISOCYANATE

[75] Inventors: Shinsuke Fukuoka; Tomonari Watanabe, both of Kurashiki, Japan

[73] Assignee: Asahi Kasei Kogyo Kabushiki Kaisha, Osaka, Japan

[21] Appl. No.: 721,696

[22] Filed: Apr. 10, 1985

[30] Foreign Application Priority Data

Apr. 26, 1984 [JP] Japan ................... 59-82858
Oct. 26, 1984 [JP] Japan .................. 59-224118

[51] Int. Cl.[4] .......................................... C07C 118/00
[52] U.S. Cl. ................................. 560/341; 560/24; 560/352
[58] Field of Search .................. 260/453 PC, 453 P

[56] References Cited

U.S. PATENT DOCUMENTS

| | | | |
|---|---|---|---|
| 3,641,092 | 2/1972 | Henry | 260/453 PC |
| 3,734,941 | 5/1973 | Sydor | 260/453 P |
| 4,003,938 | 1/1977 | Koenig et al. | 260/453 P |
| 4,195,031 | 3/1980 | Reichmann et al. | 260/453 P |
| 4,386,033 | 5/1983 | Konig et al. | 260/453 P |
| 4,388,246 | 6/1983 | Sundermann et al. | 260/453 P |

OTHER PUBLICATIONS

Chemical Communications, No. 22, pp. 828–829 (1966).
Journal of Organic Chemistry, 31, 596–597 (1966).

Primary Examiner—Dolph H. Torrence
Attorney, Agent, or Firm—Birch, Stewart, Kolasch & Birch

[57] ABSTRACT

A process for producing an aliphatic isocyanate from an aliphatic primary amine comprising a carbonylation step in which an aliphatic primary amine is allowed to react with carbon monoxide at a temperature of about 100°–250° C. in the presence of an aromatic hydroxyl compound having a pKa value of not more than about 11, molecular oxygen and a catalyst system comprising at least one member selected from palladium and rhodium metals and components thereof and at least one member selected from iodine and bromine and compounds thereof and a combined separation and recovery step comprising a pyrolysis-distillation reaction in which the mixture of carbonylated products is heated to a temperature of from about 100° to 300° C.

17 Claims, No Drawings

PROCESS FOR PRODUCING AN ALIPHATIC ISOCYANATE

BACKGROUND OF THE INVENTION (1) Field of the Invention

This invention relates to a process for producing an aliphatic isocyanate. More particularly, it pertains to a process for producing an aliphatic isocyanate from an aliphatic primary amine, carbon monoxide and molecular oxygen in a high yield.

(2) Description of the Prior Art

Heretofore, almost all aliphatic isocyanates have been produced by a reaction between aliphatic primary amines and phosgene. However, it is preferred to produce aliphatic isocyanates more simply without the use of phosgene because of several reasons, such as the high toxicity of phosgene, by-production of large quantities of corrosive hydrogen chloride, and, furthermore, the presence of difficult-to-remove hydrolyzable chlorine compounds.

On the other hand, it has been known that an aliphatic isocyanate is capable of being prepared at a yield of about 50% by reacting an aliphatic primary amine with carbon monoxide and a stoichiometric amount of palladium chloride (E. W. Stern et al, J. Org. Chem. Vol. 31, p. 596, 1966).

However, this method has been proven to be far from practical in industrial application, because an equivalent amount or more of sodium hydrogen phosphate is required as the dehydrochlorinating agent, and the reaction is not catalytic and needs a very long reaction time of from 48 to 60 hours during which time the palladium chloride is reduced to metallic palladium to stop the reaction. As a result the yield is low.

A similar reaction has also been reported in Japanese Patent Publication examined 650/1970 (and J. Tsuji et al, Chem. Commun., p. 828, 1966), but this method is also industrially impractical, for such reasons that stoichiometric amount of palladium chloride and allyl halide are employed, the reaction is not catalytic and the palladium chloride is converted to a π-allyl complex to stop the reaction. In addition the yield is very low.

Thus, in order to avoid the problems mentioned above, the present invention provides a process for producing an aliphatic isocyanate from an aliphatic primary amine without the use of phosgene.

SUMMARY OF THE INVENTION

This invention relates to a process for producing an aliphatic isocyanate from an aliphatic primary amine, which comprises:

(a) the carbonylation step in which an aliphatic primary amine is allowed to react with carbon monoxide at a temperature of about 100° to about 250° C., in the presence of an aromatic hydroxyl compound having a pKa value of not more than about 11, molecular oxygen and a catalyst system comprising:

(1) at least one member selected from palladium or rhodium metals and compounds containing palladium or rhodium, and (2) at least one member selected from iodine, bromine, and compounds containing iodine or bromine, to obtain a mixture of carbonylated products comprising an aliphatic isocyanate, as a main-product, and at least one urethane compound, as a by-product; and (b) the combined separation and recovery step comprising a pyrolysis reaction distillation in which the mixture of the carbonylated products is heated at a temperature of about 100° to about 300° C. to decompose the urethane compound present in the mixture of the carbonylated products to an aliphatic isocyanate and an aromatic hydroxyl compound, and to recover both the aliphatic isocyanate initially contained in the mixture of the carbonylated products and the aliphatic isocyanate formed by the decomposition by separating the lower boiling component of either the aliphatic isocyanate or the aromatic hydroxyl compound in a gaseous state.

In the carbonylation step of the present invention, it is one of the specific features that the desired isocyanate is produced as a main-product accompanied by at least one urethane compound as a by-product and thus the carbonylated products are obtained as a mixture of these compounds. Although the mechanism of the production of these carbonylated products is not clear, the results of the reaction can be represented by the general scheme shown below, when employing, for example, ArOH for an aromatic hydroxyl compound and $R(NH_2)_2$ for an aliphatic primary amine.

$$R(NH_2)_2 + 2CO + O_2 + (y + 2z).ArOH \longrightarrow$$
$$x.R(NCO)_2 + y.R(NHCOOAr)(NCO) +$$
$$z.R(NHCOOAr)_2 + 2.H_2O$$

wherein R represents a di-valent aliphatic group, Ar represents an aromatic group, x, y and z are 0 or positive numbers, satisfying the relationship of $x+y+z=1$, $x \neq 0$.

In the separation and recovery steps of the present invention, the urethane compounds contained in the mixture of carbonylated products are decomposed into the isocyanate compound and the aromatic hydroxyl compound.

In the present invention, the urethane compound denotes any compound having at least one urethane group formed by carbonylation of an amino group of an aliphatic primary amine, for example $R(NHCOOAr)_2$ or $R(NHCOOAr)(NCO)$ as described above, and the isocyanate compound denotes the compound having at least one isocyanate group and not having any urethane groups, for example $R(NCO)_2$ as described above.

The urethane compounds contained in the carbonylated products are the addition products of an aromatic hydroxyl compound having a pKa value of not more than about 11 to the aliphatic isocyanate, thus they are more readily decomposed thermally to the isocyanate and the aromatic hydroxyl compound compared with the urethane compounds obtained from an aliphatic alcohol and the aliphatic isocyanate. This is one of the specific features of the separation and recovery steps of the present invention. The pyrolysis reaction is represented by, for example, the scheme as shown below:

$$y.R(NHCOOAr)(NCO) + z.R(NHCOOAr)_2 \rightarrow (y+z).R(NCO)_2 + (y+2z).ArOH$$

wherein R, Ar, y, and z are the same as defined above.

DETAILED DESCRIPTION OF THE INVENTION

Any of a large selection of palladium or rhodium metals or compounds containing palladium or rhodium can be used in the catalyst system of the carbonylation step of the present invention. These catalysts may be supported on any of a number of known carriers such as active carbon, graphite, silica, alumina, silica-alumina, silica-titania, titania, zirconia, barium sulfate, calcium carbonate, asbestos, bentonite, diatomaceous earth, polymers, ion-exchange resins, zeolite, molecular sieve, magnesium silicate and magnesia, preferably on active carbon, silica, alumina or calcium carbonate. Palladium black and rhodium black or the catalysts prepared by supporting compounds containing these metal ions on a carrier and reducing them with hydrogen or formaldehyde or hydrazine can be used as metallic catalysts. Alloys and intermetallic compounds containing at least one of these metals may be employed. These may be formed between palladium and rhodium or may also contain other elements such as selenium, tellurium, sulfur, phosphorus, antimony, bismuth, copper, silver, gold, zinc, tin, vanadium, iron, cobalt, nickel, mercury, lead, thallium, chromium, molybdenum and tungsten, preferably tellurium or lead.

Exemplary compounds containing palladium or rhodium which may be employed include inorganic acid salts and their hydrates, such as the halides, sulfates, nitrates, phosphates and borates; organic acid salts and their hydrates such as the acetates, oxalates and formates; cyanides; hydroxides; oxides and their hydrates; sulfides; metal acid salts and their hydrates containing an anion such as a nitro group, a cyano group, a halogen atom and an oxalate ion; metal complexes with salts and their hydrates or complexes containing ammonia, an amine, a phosphine, a halogen atom and/or a carbon monoxide ligand; and organometallic compounds having an organic ligand or an organic group.

Preferable examples of the catalyst components include Pd black; carrier-supported palladium catalysts, such as Pd-C, Pd-Al$_2$O$_3$, Pd-SiO$_2$, Pd-TiO$_2$, Pd-ZrO$_2$, Pd-BaSO$_4$, Pd-CaCO$_3$, Pd-asbestos, Pd-zeolite and Pd-molecular sieve; alloys and intermetallic compounds, such as Pd-Pb, Pd-Se, Pd-Te, Pd-Hg, Pd-Tl, Pd-P, Pd-Cu, Pd-Ag, Pd-Fe, Pd-Co, Pd-Ni and Pd-Rh and these alloys and intermetallic compounds supported on the carrier as described above; inorganic acid salts such as PdCl$_2$, PdBr$_2$, PdI$_2$, Pd(NO$_3$)$_2$ and PdSO$_4$; organic acid salts such as Pd(OCOCH$_3$)$_2$ and palladium oxalate; Pd(CN)$_2$; PdO; PdS; palladium acid salts represented by M$_2$(PdX$_4$) and M$_2$(PdX$_6$) wherein M represents an alkali metal, an ammonium ion, X represents a nitro group or a cyano group or a halogen atom; ammine complexes represented by [Pd(NH$_3$)$_4$]X$_2$ and [Pd(en)$_2$]X$_2$ where X is the same as defined above and en represents ethylenediamine; complex compounds or organometallic compounds such as PdCl$_2$(PhCN)$_2$, PdCl$_2$(PR'$_3$)$_2$, Pd(CO)(PR'$_3$)$_3$, Pd(PPh$_3$)$_4$, PdCl(R')(PPh$_3$)$_2$, Pd(C$_2$H$_4$)(PPh$_3$)$_2$ and Pd(C$_3$H$_5$)$_2$ where R' represents an organic group and Ph represents a phenyl group; complex compounds having a coordinated chelate ligand such as Pd(acac)$_2$ where acac represents an acetylacetonato group; rhodium black; carrier-supported rhodium catalysts similar to those of Pd; rhodium alloys and intermetallic compounds which may be supported on a carrier similar to those of Pd; inorganic acid salts such as RhCl$_3$ and its hydrates, RhBr$_3$ and its hydrates, RhI$_3$, its hydrates and Rh$_2$(SO$_4$)$_3$ and its hydrates; Rh$_2$(OCOCH$_3$)$_4$, Rh$_2$O$_3$, RhO$_2$, M$_3$(RhX$_6$) and hydrates thereof wherein M and X are the same as defined above, ammine complexes of rhodium such as [Rh(NH$_3$)$_5$]X$_3$ and [Rh(en)$_3$]X$_3$; rhodium carbonyl clusters such as Rh$_4$(CO)$_{12}$ and Rh$_6$(CO)$_{16}$; complex compounds or organometallic compounds such as [RhCl(CO)$_2$]$_2$, RhCl$_3$(PR'$_3$)$_3$, RhCl(PPh$_3$)$_3$, RhX(CO)L$_2$ where R' and X are the same as defined above, L is a ligand comprising an organic phosphorous compound and an organic arsenic compound and Ph is a phenyl group; and RhH(CO)-(PPh$_3$)$_3$ where Ph is a phenyl group.

In the carbonylation step of the present invention there may be employed either one kind of metallic palladium or rhodium or compounds containing palladium or rhodium, or a mixture of two or more kinds thereof. Preferably the palladium or rhodium metal or the compound containing at least one element of the two is employed in its solid state.

The amount of the palladium or rhodium metal or compound containing palladium or rhodium which may be employed in the carbonylation step of the present invention is not particularly limited. The total amount of palladium or rhodium per se and in its compound form is typically about 0.0001 to about 50% by mol per mol of the aliphatic primary amine employed.

Any of a large selection of iodine or bromine or compounds containing iodine or bromine can be used in the carbonylation step of the present invention. The compounds containing iodine or bromine include both organic and inorganic compounds except the compounds containing palladium or rhodium, for example, metal iodides, metal bromides, onium iodides, onium bromides, compounds capable of forming onium iodides or onium bromides in the reaction system, oxo acids of iodine or their salts, oxo acids of bromine or their salts, complex compounds containing iodine, complex compounds containing bromine, organic iodides and organic bromides. Metal iodides or bromides or onium iodides or bromides or compounds capable of forming an onium iodide or bromide in the reaction system are preferable. Of these metal iodides and metal bromides, alkali metal iodides, alkali metal bromides, alkaline earth metal iodides and alkaline earth metal bromides are the most preferred, because they have excellent catalytic activities as co-catalysts, and they are able to be easily separated and recovered.

Exemplary alkali metal iodides or bromides and alkaline earth metal iodides or bromides include single salts, such as lithium iodide, sodium iodide, potassium iodide, rubidium iodide, cesium iodide, lithium bromide, sodium bromide, potassium bromide, rubidium bromide, cesium bromide, magnesium iodide, calcium iodide, strontium iodide, barium iodide, magnesium bromide, calcium bromide, strontium bromide and barium bromide; double salts such as potassium magnesium bromide; and polyhalides such as potassium bromofluoride, potassium iodochloride, rubidium iodochloride, cesium iodochloride, cesium iodochlorobromide, rubidium iodochlorobromide, potassium iodobromide, cesium iodobromide and rubidium iodobromide.

The onium iodide or bromide means a compound containing an element having a lone pair of electrons in which a proton or another cation type reagent is bonded to the lone pair of electrons to increase one covalent bond valency of the element having the lone pair of electrons to become a cation, and having an iodide or bromide ion as the counter anion. Exemplary onium iodide or bromide include ammonium compounds of the formula $(R^1R^2R^3R^4N\oplus)X\ominus$, phosphonium compounds having the formula $(R^1R^2R^3R^4P\oplus)X\ominus$, arsonium compounds having the formula $(R^1R^2R^3R^4As\oplus)X\ominus$, stibonium compounds having the formula $(R^1R^2R^3R^4Sb\oplus)X\ominus$, oxonium compounds having the formula $(R^1R^2R^3O\oplus)X\ominus$, sulfonium compounds having the formula $(R^1R^2R^3S\oplus)X\ominus$, oxysulfonium compounds having the formula $[R^1R^2R^3S\oplus(O)]X\ominus$, selenonium compounds having the formula $(R^1R^2R^3Se\oplus)X\ominus$, telluronium compounds having the formula $(R^1R^2R^3Te\oplus)X\ominus$, stannonium compounds $(R^1R^2R^3Sn\oplus)X\ominus$ and iodonium compounds having the formula $(R^1R^2I\oplus)X\ominus$. In these formulae, $R^1$, $R^2$, $R^3$ and $R^4$ each independently represents a hydrogen atom or a group selected from the group consisting of aliphatic groups, aromatic groups, alicyclic groups, arylaliphatic groups and heterocyclic groups which may sometimes be a constituent of a ring containing an element having a lone pair of electrons; and X represents I or Br. Compounds having two or more of such onium groups in the molecule and further polymers containing such onium groups in the main chain or a side chain thereof may also be employed.

The instant onium iodides or bromides can be readily obtained by the reaction of hydrogen iodide or hydrogen bromide or an organic iodide or bromide with the counterpart amine, nitrogen-containing compound, phosphine compound, arsine compound, stibine compound, oxy compound, sulfide compound, sulfoxide compound, selenide compound or telluride compound. These onium iodides or bromides may be formed either outside the reaction system or in the reaction system. Furthermore, onium iodides or bromides prepared according to other methods may also be utilized and they may be formed in the reaction system according to other methods.

Of these onium iodides or bromides, ammonium iodides, ammonium bromides, phosphonium iodides, phosphonium bromides, sulfonium iodides, sulfonium bromides, iodonium iodides and iodonium bromides are preferred, and ammonium iodides or bromides and phosphonium iodides or bromides are the most preferred, because they have excellent catalytic activities as co-catalysts, and they are able to be easily separated and recovered.

An ammonium iodide or bromide can be readily obtained by the reaction of a corresponding nitrogen-containing compound with hydrogen iodide or hydrogen bromide or the reaction of a nitrogen-containing compound with an alkyl iodide or bromide or an aryl iodide or bromide. Exemplary hydrogen iodide or bromide salts of nitrogen-containing compounds which can be employed include the salts of ammonia such as ammonium iodide and ammonium bromide; the salts of aromatic amines such as diphenylamine and triphenylamine; the salts of aliphatic amines such as methylamine, ethylamine, n-hexylamine, n-octylamine, dimethylamine, trimethylamine, diethylamine, triethylamine, di-n-butylamine, tri-n-propylamine, methylethylamine, dimethylethylamine, di-n-butylmethylamine, tri-n-butylamine, ethylenediamine and hexamethylenediamine; the salts of alicyclic amines such as cyclopropylamine, cyclohexylamine and N-methylcyclohexylamine; the salts of arylaliphatic amines such as benzylamine, N-methylbenzylamine, N,N-diethylbenzylamine and dibenzylamine; the salts of nitrogen-containing heterocyclic compounds such as piperidine, piperazine, morpholine, pyridine, quinoline, hexamethylenetetramine, oxazole, thiazole, imidazole, triazole, benzotriazole and diazabicycloundecene; and the salts of amides such as dimethylacetamide and N-methylpyrrolidone.

Exemplary quarternary ammonium iodides or bromides which can be employed include aliphatic quarternary ammonium iodides or bromides such as tetramethylammonium iodide, tetramethylammonium bromide, tetraethylammonium iodide, tetraethylammonium bromide, tetra-n-butylammonium iodide, tetra-n-butylammonium bromide, ethyltrimethylammonium iodide, ethyltrimethylammonium bromide, diethyldibutylammonium iodide, diethyldibutylammonium bromide; alicyclic quarternary ammonium iodides or bromides such as cyclohexyltrimethylammonium iodide, cyclohexyltrimethylammonium bromide; arylaliphatic quarternary ammonium iodides or bromides such as tetrabenzylammonium iodide, tetrabenzylammonium bromide, benzyltrimethylammonium iodide, benzyltrimethylammonium bromide; aromatic quarternary ammonium iodides or bromides such as phenyltrimethylammonium iodide, phenyltrimethylammonium bromide, phenyltriethylammonium iodide, phenyltriethylammonium bromide; and heterocyclic quarternary ammonium halides such as N-methylpyridinium iodide, N-methylpyridinium bromide, N-ethylquinolinium iodide, N-ethylquinolinium bromide, N,N-dimethylpiperidinium iodide, N,N-dimethylpiperidinium bromide, N,N'-dimethylimidazolinium iodide and N,N'-dimethylimidazolinium bromide.

Exemplary phosphonium iodides or bromides which can be used include symmetric tetraalkylphosphonium iodides or bromides such as tetramethylphosphonium iodide, tetramethylphosphonium bromide, tetraethylphosphonium iodide, tetraethylphosphonium bromide, tetra-n-butylphosphonium iodide, tetra-n-butylphosphonium bromide; asymmetric tetraalkylphosphonium iodides or bromides such as ethyltrimethylphosphonium iodide, ethyltrimethylphosphonium bromide, diethyldimethylphosphonium iodide, diethyldimethylphosphonium bromide; symmetric tetraarylphosphonium iodides or bromides such as tetraphenylphosphonium iodide, tetraphenylphosphonium bromide, tetra(p-tolyl)phosphonium iodide, tetra(p-tolyl)phosphonium bromide; asymmetric tetraarylphosphonium iodides or bromides such as (α-naphthyl)triphenylphosphonium iodide, (α-naphthyl)triphenylphosphonium bromide; alkyl/aryl mixed phosphonium iodies or bromides such as methyltriphenylphosphonium iodide, methyltriphenylphosphonium bromide, phenyltrimethylphosphonium iodide, phenyltrimethylphosphonium bromide; and tetraaralkylphosphonium iodies or bromides such as tetrabenzylphosphonium iodide, tetrabenzylphosphonium bromide.

The oxo acids of iodine or bromine and their salts mean oxygen acids of iodine or bromine having an oxidation number of $+1$, $+3$, $+5$ or $+7$ and their salts. Exemplary oxo acids of iodine or bromine and their salts which can be employed include hypoiodous acid, iodus acid, iodic acid, orthoperiodic acid, methaperiodic acid, hypobromous acid, bromic acid, perbromic acid and their salts. The cations of the salts which can be employed may be any cations such as an ammonium ion and various metallic ions, and preferred cations are alkali metal ions and alkaline earth metal ions.

Exemplary salts of the oxo acids of iodine or bromine which can be employed include the hypoiodites such as sodium hypoiodite, potassium hypoiodite, rubidium hypoiodite, cesium hypoiodite, calcium hypoiodite and barium hypoiodite; the iodates such as lithium iodate, sodium iodate, potassium iodate, potassium hydrogen iodate, rubidium iodate, cesium iodate, magnesium iodate, calcium iodate, strontium iodate, barium iodate, and ammonium iodate; the periodates such as lithium periodate, sodium methaperiodate, dihydrogentrisodium orthoperiodate, trihydrogendisodium orthoperiodate, potassium methaperiodate, trihydrogendipotassium orthoperiodate, hydrogentripotassium dimesoperiodate, rubidium periodate, cesium periodate, barium periodate, and ammonium periodate; the hypobromites such as sodium hypobromite and potassium hypobromite; the bromites such as sodium bromite; the bromates such as lithium bromate, sodium bromate, potassium bromate, rubidium bromate, cesium bromate, magnesium bromate, calcium bromate, strontium bromate, barium bromate, and ammonium bromate; the perbromates such as potassium perbromate.

The complex compounds containing iodine or bromine ions may be either cationic or anionic iodine- or bromine-containing complex compounds. Exemplary complex compounds containing iodine or bromine ions include halogenic acid polyhalide salts such as ammonium dichlorobromate and tetramethylammonium tetrabromoiodate; metal acid halide salts such as potassium hexaiodotellurate, tetramethylammonium tetraiodomercurate, potassium tetraiodoplumbate and potassium hexabromotellurate; complexes having ligands such as tetrabromo(diethylsuccinate)tin, octates(N,N-dimethylformamide)lanthantriiodide.

The organic iodides or bromides which can be employed in this invention is represented by the formula:

$R^6(X')_m$ wherein $R^6$ is an organic group having a valency of m; $X'$ is I or Br, and m is an integer of 1 or more.

When m is 2 or more, $X'$ may be two or more kinds of different halogen atoms. The halogen atom $X'$ may also be bonded to a hetero atom other than carbon such as nitrogen, phosphorus, oxygen, sulfur or selenium.

The above described iodine or bromine or compounds containing iodine or bromine may be used as a single species or two or more species as a mixture. Of the iodine or bromine or compounds containing iodine or bromine which can be used in the carbonylation step of this invention, iodine or the compounds containing iodine are more preferred.

The amount of the iodine or bromine or compound containing iodine or bromine which can be employed is not particularly limited, and the total amount of the iodine and bromine atom in the calbonylation catalyst system is typically about 0.001 to about 10000 mols per the total amount of palladium and rhodium atom in that catalyst system. Of these catalyst sytems which can be used in the carbonylation step of the present invention, the systems consisting of palladium metal or palladium-containing compounds as main catalysts and iodine or iodine-containing compounds as promoters are particularly preferred.

Any of a large selection of the aromatic hydroxyl compounds in which the hydroxyl group is directly bonding to the aromatic ring can be used in this invention, so far as the pKa value of the hydroxyl group is about 11 or less. In the present invention, it is found that the use of the aromatic hydroxyl compound having the pKa value of about 11 or less gives the isocyanate as a main product in the carbonylation step. If the aromatic hydroxyl compound having the pKa value of more than about 11 is used, the urethane compound is obtained as a main product in the step. So, in order to obtain the isocyanate as a main product in the carbonylation step, it is important to use the aromatic hydroxyl compound which pKa value is about 11 or less. In this sense, the use of the aromatic hydroxyl compound having the pKa value of about 10.5 or less is more preferred.

The aromatic hydroxyl compounds used in the present invention include phenol or a substituted phenol having at least one substituent selected from the group consisting of $C_1 \sim C_{10}$ alkyl group, $C_6 \sim C_{18}$ aryl group, $C_7 \sim C_{15}$ aralkyl group, nitro group, cyano group and halogen atom, naphthol or a substituted naphthol, a heteroaromatic hydroxyl compound, an aromatic dihydroxy compound and the like.

Exemplary aromatic hydroxyl compounds include phenol; alkyl phenols such as cresol (respective isomers), xylenol (respective isomers), ethylphenol (respective isomers), propylphenol (respective isomers); halogenated phenols such as chlorophenol (respective isomers), bromophenol (respective isomers), dichlorophenol (respective isomers), dibromophenol (respective isomers); phenols having both alkyl group and halogen such as methylchlorophenol (respective isomers), ethylchlorophenol (respective isomers), methylbromophenol (respective isomers), ethylbromophenol (respective isomers); nitrophenols (respective isomers), cyanophenols (respective isomers); substituted phenols represented by the formula:

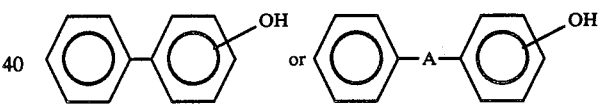

wherein

A represents a divalent group such as —O—, —S—, —SO$_2$—, —CO—, —CH$_2$— and —C(R'')$_2$—(R'' represents a lower alkyl group), and the aromatic rings may be substituted by other groups such as halogen, alkyl group, ester group, amide group and cyano group;

naphthols (respective isomers) and various substituted naphthols such as cyanonaphthols (respective isomers), nitronaphthols (respective isomers); heteroaromatic hydroxyl compounds such as hydroxypyridine (respective isomers), hydroxycumarin (respective isomers), hydroxy-quinoline (respective isomers); aromatic dihydroxy compounds such as dihydroxybenzene (respective isomers), dihydroxynaphthalene (respective isomers), and those of substituted by alkyl group or halogen; aromatic dihydroxy compounds represented by the formula:

or

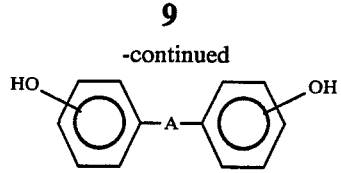

wherein

A is the same described before, and aromatic rings may be substituted by other groups such as halogen, alkyl group, ester group, amide group and cyano group;

A preferred aromatic hydroxyl compound has a difference in boiling point by at least 10° C. from the desired aliphatic isocyanate under the pyrolysis reaction distillation conditions. In one preferable working mode of the present invention, it is preferred to use an aromatic hydroxyl compound having a boiling point higher by at least 10° C. from the desired aliphatic isocyanate under the pyrolysis reaction distillation conditions. In this case, the aliphatic isocyanate can be separated as the gas phase component, while the higher boiling compounds containing the aromatic hydroxyl compound are recovered as the liquid phase component and thereafter reused as such or after some purification in the carbonylation step, and it is not also required to separate the aromatic hydroxyl compound existing in excessive amount before the pyrolysis reaction distillation. Such aromatic hydroxyl compounds may be used either alone or as a mixture of two or more compounds.

In the carbonylation step, the aromatic hydroxyl compound should be employed preferably in an amount such that the hydroxyl group may be one mole or more per mole of the amino group of the primary amine employed. A more preferable amount to be used corresponds to 5 moles or more, further preferably 10 moles or more, of hydroxyl groups per mole of the amino group. If the amount of the aromatic hydroxyl group is less than one mole per amino group of the primary amine, urea compounds will undesirably be produced as a by-product.

The aliphatic primary amine to be used in the present invention may be any one containing one or more primary amino groups bonded to an aliphatic carbon atom or aliphatic carbon atoms, which may be also inclusive of alicyclic primary amines and arylaliphatic primary amines. Examples of such aliphatic primary monoamines and polyamines may include aliphatic primary monoamines, such as methylamine, ethylamine, propylamine (respective isomers), butylamine (respective isomers), pentylamine (respective isomers), hexylamine (respective isomers), and dodecylamine (respective isomers); aliphatic primary diamines, such as ethylenediamine, diaminopropane (respective isomers), diaminobutane (respective isomers), diaminopentane (respective isomers), diaminohexane (respective isomers), and diaminodecane (respective isomers); aliphatic primary triamines, such as 1,2,3-triaminopropane, triaminohexane (respective isomers), triaminononane (respective isomers), triaminododecane (respective isomers), 1,8-diamino-4-aminomethyl-octane, 2-aminoethyl-2,6-diaminocaproate, 1,3,6-triaminohexane, and 1,6,11-triaminoundecane; alicyclic primary mono- and poly-amines, such as cyclopropylamine, cyclobutylamine, cyclopentylamine, cyclohexylamine, diaminocyclobutane, diaminocyclohexane (respective isomers), 3-aminomethyl-3,5,5-trimethylcyclohexylamine, and triaminocyclohexane (respective isomers); arylaliphatic primary mono- and poly-amines, such as benzylamine, di(aminomethyl)benzene (respective isomers), aminomethylpyridine (respective isomers), di(aminomethyl)pyridine (respective isomers), aminomethylnaphthalene (respective isomers), and di(aminomethyl)naphthalene (respective isomers).

In the aliphatic group, the alicyclic group and the arylaliphatic group forming the skelton of these primary amines, a part of hydrogen atoms may be substituted with substituents such as a halogen, alkyl group, alkoxy group, aryl group, cyano group, ester group, and sulfone group. The skelton may also contain an unsaturated bond, ether bond, ester bond, thioether bond, sulfone bond, and ketone bond.

In the carbonylation step of the present invention, it is preferred to use an aromatic hydroxyl compound as the solvent, but other appropriate solvents may also be added. As such solvents, there may be included aliphatic hydrocarbons such as pentane, hexane, heptane, octane, and decane; alicyclic hydrocarbons, such as cyclohexane, tetralin, and decalin; aromatic hydrocarbons, such as benzene, toluene, xylene, and mesitylene; nitriles, such as acetonitrile, and benzonitrile; sulfones, such as sulforane, methylsulforane, and dimethylsulforane; ethers, such as tetrahydrofuran, 1,4-dioxane, and 1,2-dimethoxyethane; ketones, such as acetone, and methyl ethyl ketone; esters, such as ethyl acetate, and ethyl benzoate.

Further, it is possible to use a solvent selected from halogenated aromatic hydrocarbons, such as chlorobenzene, dichlorobenzene, trichlorobenzene, fluorobenzene, chlorotoluene, chloronaphthalene, and bromonaphthalene; halogenated aliphatic hydrocarbon or halogenated alicyclic hydrocarbons, such as chlorohexane, chlorocyclohexane, trichlorotrifluoroethane, methylene chloride, and carbon tetrachloride.

The carbon monoxide which can be employed as one starting material in the present invention may be pure carbon monoxide or may contain other gases, such as nitrogen, argon, helium, carbon dioxide, a hydrocarbon or a halogenated hydrocarbon. A small amount, i.e., less than about 10% by mol of hydrogen based on carbon monoxide does not affect adversely the carbonylation using the catalyst system of the instant invention, and accordingly in this invention carbon monoxide containing such a small amount of hydrogen may be advantageously employed from the industrial viewpoint.

The amount of carbon monoxide which can be employed is typically at least one mol, preferably about 2 to about 1000 mols per amino group of the primary amine.

The molecular oxygen to be used in the carbonylation step of the present invention may be pure oxygen or a component containing oxygen, which may be air or a mixture of air or pure oxygen diluted with other gases which do not interfere with the reaction, for example, inert gases, such as nitrogen, argon, helium, and carbon dioxide. In some cases, gases, such as hydrogen, carbon monoxide, hydrocarbon, and halogenated hydrocarbon may also be present.

The carbonylation step of the present invention is practiced at a temperature of about 100° to about 250° C., preferably about 150° to about 190° C. If the reaction temperature is lower than about 100° C., the production of urethane compounds or urea compounds will increase, or the reaction is too slow or does not proceed, so as to be unfavorable for industrial application, while a temperature higher than about 250° C. will produce side reactions to lower undesirably the yield of isocyanate.

The reaction pressure may be within the range of from 1 to 500 kg/cm$^2$, preferably from 20 to 300 kg/cm$^2$, and the reaction time, which may differ depending on the reaction system, the catalyst system and other reaction conditions, may generally range from several minutes to several hours.

The carbonylation reaction may be practiced either by a batchwise system or by a continuous sytem in which the reaction mixture is continuously withdrawn while supplying the reactants continuously.

In the carbonylation step, it is also possible to add other additives into the reaction system, if desired, in order to carry out the reaction more efficiently. As such additives, for example, molecular sieves having dehydrating effect are particularly preferred.

In the carbonylation step, water is generally produced as a by-product. This water may be removed from the reaction system during or after the carbonylation. It is also possible to remove it in the subsequent process.

Further, the catalyst used in the carbonylation reaction may be present in the mixture of the carbonylated products, depending on the reaction method and in such a case, the catalyst may be also removed after the carbonylation reaction or in the subsequent process.

The "second step" of the present invention includes the separation and recovery phase comprising the pyrolysis reaction distillation in which the mixture of the carbonylated product is heated at a temperature of from 100° to 300° C. to decompose the urethane compounds present in the mixture of the carbonylated products to the aliphatic isocyanate and the aromatic hydroxyl compound, and to recover both the aliphatic isocyanate initially contained in the mixture of the carbonylated products and the aliphatic isocyanate formed by the decomposition by separating of the lower boiling component of either the aliphatic isocyanate or the aromatic hydroxyl compound in a gaseous state.

In the carbonylated products produced in the carbonylation step, the aliphatic isocyanate compound is a main component, and a part thereof may be separated prior to the pyrolysis reaction distillation of the urethane compounds, or alternatively, it can preferably be introduced together with the urethane compounds, as such, into the pyrolysis reaction distillation device, and separated by distillation together with the same aliphatic isocyanate compound formed by pyrolysis. Also, in the carbonylation step, the aromatic hydroxyl compound is generally used in excess, and therefore it exists after the reaction as a mixture with the carbonylated products. The carbonylated products separated from this mixture may be introduced into the pyrolysis reaction distillation device, or alternatively the mixture, as such without separation, may be introduced into the pyrolysis reaction distillation device to effect separation into the aliphatic isocyanate compound and the aromatic hydroxyl compound.

In the pyrolysis reaction distillation, the mixture of the carbonylated products may be heated at a temperature of about 100° to about 300° C., preferably about 120° to about 270° C. If the heating temperature is lower than about 100° C., the decomposition reaction of the urethane compounds is slow or does not proceed so as to be unfavorable for industrial application, while a heating temperature higher than about 300° C. will cause side reactions to lower undesirably the yield of isocyanate.

The reaction time of the pyrolysis reaction distillation depends on the urethane compounds to be decomposed, the solvent, the catalyst employed and the reaction temperature, but it may generally run from several minutes to some ten hours, preferably several minutes to several hours, optimally as short as possible.

Since the pyrolysis reaction distillation can be practiced under any of atmospheric, reduced or pressurized system, it is possible to employ the reaction pressure which may be determined depending on the urethane compounds to be decomposed, whether the aromatic hydroxyl compound is co-present or not and whether and what kind of solvent is present or not.

For the purpose of lowering the temperature of the pyrolysis reaction or enhancing the reaction rate, a pyrolysis catalyst may also be employed. As such a catalyst, there may preferably be employed, for example, metals of rare earth elements, antimony or bismuth and oxides, sulfides and salts of these elements; boron and boron compounds; metals of the copper group, the zinc group, the aluminum group, the carbon group and titanium group of the periodic table and oxides and sulfides of these metals; and carbides and nitrides of the carbon group except for carbon, the titanium group, the vanadium group and the chromium group elements of the periodic table.

In the case of employing catalysts, the ratio of these catalysts to the urethane compounds may take any desired value, but it is preferred to use about 0.0001 to about 100-fold of catalysts relative to the weight of the urethane compounds.

In the pyrolysis reaction distillation, it is possible to use a solvent which is inert to the isocyanate compound, and such a method may sometimes be preferable. As such a solvent, there may be employed aliphatic, alicyclic or aromatic substituted or unsubstituted hydrocarbons and mixtures thereof, and some oxygen-containing compounds such as ethers, ketone and esters may also be included. Preferred solvents may include alkanes such as hexane, heptane, octane, nonane, decane, n-hexadecane, n-octadecane, eicosane, and squalane, and alkenes corresponding thereto; aromatic hydrocarbons and alkyl-substituted aromatic hydrocarbons, such as benzene, toluene, xylene, ethylbenzene, cumene, diisopropylbenzene, dibutylbenzene, naphthalene, lower-alkyl-substituted naphthalene, and dodecylbenzene; aromatic compounds substituted with nitro group and halogen, such as chlorobenene, dichlorobenzene, bromobenzene, dibromobenzene, chloronaphthalene, bromonaphthalene, nitrobenzene, and nitronaphthalene; polycyclic hydrocarbon compounds, such as diphenyl, substituted diphenyl, diphenylmethane, terphenyl, anthracene, phenanthrene, and dibenzyltoluene, alicyclic hydrocarbons, such as cyclohexane, and ethylcyclohexane; ketones, such as methyl ethyl ketone, and acetophenone; esters such as dibutylphthalate, dihexylphthalate, and dioctylphthalate; and ethers, such as diphenylether.

In the separation and recovery phase comprising the pyrolysis reaction distillation, the urethane compounds are converted into the corresponding isocyanate compound and the aromatic hydroxyl compound, and the component having a lower boiling point of these components is recovered in a gaseous state. For promoting such a separation, it is preferred to introduce an inert gas, such as nitrogen, helium, argon, carbon dioxide, methane, ethane, and propane either alone or as a mixture into the reaction system. As the material having a similar action, it is also possible to use organic compounds with low boiling points, including halogenated hydrocarbons, such as dichloromethane, chloroform, and carbon tetrachloride; lower hydrocarbons, such as pentane, hexane, heptane, and benzene; and ethers, such as tetrahydrofuran, and dioxane.

The mode of the reactor used in the separation and recovery phase is not particularly limited, and it is preferable to use the method in which pyrolysis is effected by means of a vertical type tubular reactor wherein as the carbonylated products flow down therethrough to decompose the urethane compounds, the lower boiling element of either the aliphatic isocyanate or the aromatic hydroxyl compound existing in the system is taken out in a gaseous state from the upper part of the reactor and the higher boiling component is taken out from the lower part of the reactor, to be recovered separately; the method by means of a tank reactor in which the lower boiling product is recovered in gaseous state; and the method in which these methods are combined. Further, if desired, a distillation tower and/or partial condenser may also be provided at the upper part of these pyrolysis reactors. This separation and recovery step may be practiced either by batchwise system or by continuous system.

Thus, in the present invention, the specific feature resides in combinating the carbonylation step for producing the mixture of carbonylated products comprising an aliphatic isocyanate, as a main-product and at least one urethane compound, as a by-product, with the separation and recovery step in which the urethane compounds are decomposed into the aliphatic isocyanate and the aromatic hydroxyl compound and the lower boiling component is recovered in gaseous state through pyrolysis reaction distillation.

Accordingly, the process of the present invention clearly has the following advantages when practiced in an industrial environment:

(1) The urethane compounds by-produced in the carbonylation step are the compounds prepared by the addition of an aromatic hydroxyl compound with a pKa of about 11 or less to an aliphatic isocyanate, thus they don't need so high temperature to be pyrolyzed as the urethane compounds prepared by the addition of an aromatic hydroxyl compound with a pKa greater than about 11 do, and furthermore they are able to be easily pyrolyzed at lower temperature compared with the urethane compounds prepared by the addition of aliphatic alcohols to the isocyanate need a high temperature about 300° C. or more to be pyrolyzed. Therefore the side reactions which will readily occur at higher temperatures are depressed and the isocyanate compound is able to be obtained in a high yield;

(2) Since the pyrolysis reaction distillation system is employed, in which the isocyanate compound formed by pyrolysis is separated simultaneously with the formation from the aromatic hydroxyl compound, the residence time at the pyrolysis temperature is short, whereby the formation of polymeric materials through the side reaction of the isocyanate compound is depressed to produce the isocyanate compound in higher yield;

(3) Since the pyrolysis temperature is low, the pyrolysis does not need large quantities of the heat energy;

(4) The urethane compounds to be pyrolyzed are the by-products in the carbonylation step, which are small in amount, and therefore the quantities of the heat energy required for pyrolysis is able to be small; and (5) The mixture of the carbonylated products may be pyrolyzed prior to the separation of the aliphatic isocyanate produced, an aromatic hydroxyl compound remained or a catalyst or a solvent used in the carbonylation step.

The process of the present invention is suitable for the production of aliphatic monoisocyanates, aliphatic diisocyanates and aliphatic polyisocyanates, and it is also a process suitable for the production of hexamethylene diisocyanate which is used in large amounts in industry.

The present invention is described in more complete detail by reference to the following Examples, which are given by way of illustration only, and are not intended to limit, in any way, the scope of the present invention.

EXAMPLE 1

Into a stirring type 200 ml autoclave are charged 12.5 mmol of hexamethylenediamine, 47 g of phenol, 0.5 mg atom of palladium black and 1 mmol of sodium iodide. After the air inside the autoclave has been replaced with carbon monoxide, 75 kg/cm$^2$ of carbon monoxide and then 35 kg/cm$^2$ of air are pressurized into the autoclave to a total pressure of 110 kg/cm$^2$. After the carbonylation reaction is carried out under stirring at 170° C. for one hour, the reaction mixture is filtered to recover the total amount of the palladium black by separation.

As the result of analysis of the reaction mixture, it is found that the conversion of hexamethylenediamine is 100%, with formation of hexamethylene diisocyanate in a yield of 73%, 1-isocyanate-6-phenoxycarbamoyl-hexane which is a monoisocyanate monourethane in a yield of 14% and 1,6-diphenoxycarbamoyl-hexane which is a diurethane in a yield of 7%.

When no sodium iodide is employed, the carbonylation reaction does not substantially proceed.

Next, into a simple distillation device comprising a three-necked flask equipped with a thermometer, a nitrogen inlet extending to below the liquid level and a Liebig's cooler is charged the reaction mixture obtained in the carbonylation step, and nitrogen is introduced at 30 liters/hour with the outer bath of the flask being heated to 200° C. Water and most of phenol formed in the carbonylation reaction evaporates at the temperatures up to 185° C. During this operation, the pyrolysis reaction is also found to proceed at the same time, and further the outer bath temperature increases to 210° C. and is maintained thereafter for 10 minutes for a pyrolysis reaction distillation, whereby the phenol formed by decomposition substantially completely evaporates. The phenol is recovered at approximately 100%. The residue obtained is subjected to vacuum distillation to obtain 1.95 g of hexamethylene diisocyanate distilled at 126°–127° C./10 mm Hg (yield 92.8% based on hexamethylenediamine).

EXAMPLE 2

As the result of the carbonylation reaction conducted in the same manner as in Example 1 except for employing 54 g of p-cresol in place of phenol, the conversion of hexamethylenediamine is found to be 100%, with formation of hexamethylene diisocyanate in a yield of 62%, 1-isocyanate-6-(p-methylphenoxy)carbamoyl-hexane in a yield of 3% and di-(p-methylphenoxy)carbamoylhexane in a yield of 30%.

The reaction mixture from which palladium black is removed is subjected to a pyrolysis reaction simultaneously with distillation of p-cresol according to the same method as in Example 1, by maintaining the outer bath temperature of the flask at 210° C. After substantially almost all the amount of p-cresol is recovered, the residue is distilled under reduced pressure to obtain 1.93 g of hexamethylene diisocyanate distilled at 126°–127° C./10 mm Hg (yield 91.9% based on hexamethylenediamine).

EXAMPLE 3

As the result of the carbonylation reaction carried out in the same manner as in Example 1 except for using 55 g of p-chlorophenol in place of phenol and 1 mmol of tetramethylammonium iodide in place of sodium iodide, the conversion of hexamethylenediamine is found to be 100%, with formation of hexamethylene diisocyanate in a yield of 75%, 1-isocyanate-6-(p-chlorophenoxy)carbamoyl-hexane in a yield of 15% and di-(p-chlorophenoxy)carbamoyl-hexane in a yield of 5%.

The reaction mixture from which palladium black is removed is placed in the same three-necked flask, as used in Example 1. In this case, however, the nitrogen inlet employed is a capillary tube and the whole system is kept under 300 mm Hg. While maintaining the outer bath temperature of the flask at 220° C., pyrolysis reaction is practiced simultaneously with distillation of p-chlorophenol. After recovery of substantially almost all the amount of p-chlorophenol, the residue is distilled under reduced pressure to obtain 1.94 g of hexamethylene diisocyanate distilled at 126°–127° C./10 mm Hg (yield 92.4% based on hexamethylenediamine).

EXAMPLES 4–10

Carbonylation reaction and pyrolysis reaction distillation are carried out according to the same procedure as in Example 1 except for using various halogen compounds, as shown in Table 1, in place of sodium iodide, and hexamethylene diisocyanate is obtained by vacuum distillation.

The results are shown in Table 1.

Here, HMDI, HMIU, and HMDU represent respectively hexamethylene diisocyanate, 1-isocyanate-6-phenoxycarbamoyl-hexane, and 1,6-diphenoxycarbamoyl hexane. The yields are values based on hexamethylenediamine used.

TABLE 1

| Example | Halogen compound (mmol) | Carbonylation yield (%) HMDI | HMIU | HMDU | HMDI yield after pyrolysis (%) |
|---|---|---|---|---|---|
| 4 | CHI$_3$ (0.4) | 50 | 8 | 3 | 55 |
| 5 | KBrO$_3$ (1) | 58 | 11 | 5 | 70 |
| 6 | KIO$_4$ (1) | 70 | 13 | 8 | 83 |
| 7 | K$_2$[TeBr$_6$] (0.2) | 52 | 7 | 5 | 57 |
| 8 | [(C$_6$H$_5$)$_3$PCH$_3$] (1) | 74 | 12 | 8 | 85 |
| 9 | CsI (1) | 71 | 16 | 7 | 90 |
| 10 | I$_2$(1) + (C$_2$H$_5$)$_3$N(5) | 44 | 7 | 3 | 48 |

EXAMPLE 11

According to the same procedure as in Example 1, except for using 80 g of p-phenylphenol in place of phenol, carbonylation reaction is carried out to obtain hexamethylene diisocyanate in a yield of 66%, 1-isocyanate-6-(p-phenylphenoxy)carbamoyl-hexane in a yield of 18% and 1,6-di-(p-phenylphenoxy)carbamoylhexane in a yield of 10%.

The carbonylation reaction mixture is subjected to pyrolysis reaction and distillation separation practiced similarly as in Example 3. While maintaining the flask bath temperature at 210° C. and the pressure within the system at 150 mm Hg, hexamethylene diisocyanate formed by pyrolysis is distilled out, to obtain 1.89 g of hexamethylene diisocyanate (yield 90% based on hexamethylene diamine).

EXAMPLE 12

After the carbonylation reaction is conducted in one liter autoclave similarly as in Example 1 using 7.3 g of n-butylamine, 500 g of p-chlorophenol, 10 mmol of sodium iodide, 15 g of Pd/SiO$_2$ having 2% Pd carried on silica gel, Pd/SiO$_2$ is removed by filtration. As the result of analysis of the reaction mixture, it is found that the conversion of n-butylamine is 100%, with formation of n-butyl isocyanate in a yield of 80% and (p-chlorophenyl)methylcarbamate in a yield of 14%. The resultant mixture is introduced at a flow rate of 100 g/hour from the upper part of a vertical tubular type reactor (diameter: 2 cm, length: 1 m, filled with Dixon packings) maintained at 210° C. From the lower part of the reactor, nitrogen gas pre-heated at 150° C. is introduced at a rate of 10 liter/hour. The reactor tube is also equipped at the upper part with a partial condenser maintained at 140° C. N-butyl isocyanate formed with the progress of the reaction is taken out in gaseous state from the upper part of the partial condenser and cooled through a water-cooled cooler to be recovered in a liquid state. The yield of n-butyl isocyanate is found to be 92% based on n-butylamine used.

EXAMPLE 13

The carbonylation reaction is conducted in the same manner as in Example 1 except that 25 mmol of cyclohexylamine, 86 g of α-naphthol, 1.5 g of Rh/C having 5% Rh carried on activated charcoal and 1 mmol of tetraethylammonium iodide are employed. As a result, the yields of cyclohexyl isocyanate and α-naphthyl cyclohexyl carbamate are 58% and 10%, respectively.

The reaction mixture from which Rh/C is removed by filtration is placed in a three-necked flask to be subjected to pyrolysis reaction simultaneously with distillation of cyclohexyl isocyanate according to the following method. The flask has a nitrogen inlet extending to below the liquid level, a thermometer and a partial condenser and is maintained at 205° C. by an outer bath. The partial condenser is maintained at 185° C.

While the nitrogen preheated at 180° C. is introduced at 20 l/hour into the reaction mixture, both cyclohexyl isocyanate contained in the carbonylation reaction mixture and the same formed by pyrolysis are taken out in gaseous state together with small amounts of vapor of α-naphthol from the upper part of the partial condenser and cooled to be recovered in liquid state. The yield of cyclohexyl isocyanate is found to be 66% based on cyclohexyl amine used.

EXAMPLE 14

In the same manner as in Example 1, the carbonylation reaction mixture is obtained, with the formation of hexamethylene diisocyanate, 1-isocyanate-6-phenoxycarbamoyl-hexane and 1,6-diphenoxy-carbamoylhexane in yields of 78%, 12% and 6%, respectively.

This reaction mixture is found to have a composition by weight comprising 10.7% of hexamethylene diisocyanate, 2.6% of 1-isocyanate-6-phenoxycarbamoylhexane, 1.7% of 1,6-diphenoxy carbamoyl-hexane and 82% of phenol.

The resultant mixture preheated at 160° C. is introduced at a flow rate of 40 g/min. from the middle part of a vertical tubular type reactor (diameter: 5 cm, length: 4 m, filled with Dixon packings).

The lower part of the reactor than the inlet of the reaction mixture is maintained at 210° C. and its upper part than the inlet of the reaction mixture is maintained at 190° C.

From the upper part of the reactor, both the phenol initially contained in the mixture fed and the phenol formed by pyrolysis of the urethane compounds are recovered almost quantitatively.

The liquid product obtained from the lower part of the reactor is found to contain 96% of hexamethylene diisocyanate.

The invention being thus described, it will be obvious that the some may be varied in many ways. Such variations are not to be regarded as a departure from the spirit and scope of the present invention, and all such modifications as would be obvious to one skilled in the art are intended to be included within the scope of the following claims.

We claim:

1. A process for producing an aliphatic isocyanate from an aliphatic primary amine, which comprises:
   (a) a carbonylation step in which an aliphatic primary amine is allowed to react with carbon monoxide at a temperature of about 100 to about 250° C. in the presence of an aromatic hydroxyl compound having a pKa value of not more than 11, molecular oxygen and a catalyst system comprising:
      (1) at least one member selected from palladium and rhodium metals and compounds containing palladium or rhodium and
      (2) at least one member selected from iodine and bromine and compounds containing iodine or bromine,
   to obtain a mixture of carbonylated products comprising an aliphatic isocyanate as a main-product and at least one urethane compound as a by-product; and
   (b) separating and recovering said aliphatic isocyanate comprising a pyrolysis reaction-distillation in which said mixture of carbonylated products is heated at a temperature of from about 100° to about 300° C. to decompose said at least one urethane compound present in said mixture of carbonylated products to an aliphatic isocyanate and an aromatic hydroxyl compound, and recovering both said aliphatic isocyanate initially contained in said mixture of carbonylated products and said aliphatic isocyanate formed by decomposition of said urethane compound by separating the lower boiling component of either of said the aliphatic isocyanate or said aromatic hydroxyl compound in gaseous state.

2. A process according to claim 1, wherein said aromatic hydroxyl compound is phenol or a substituted phenol having at least one substituent selected from the group consisting of $C_1 \sim C_{10}$ alkyl group, $C_6 \sim C_{18}$ aryl group, $C_7 \sim C_{15}$ aralkyl group, nitro group, cyano group and halogen atom.

3. A process according to claim 1, wherein said aromatic hydroxyl compound is a naphthol or a substituted naphthol.

4. A process according to claim 1, wherein said aromatic hydroxyl compound has a difference in boiling point by at least 10° C. from said aliphatic isocyanate under said pyrolysis reaction distillation condition.

5. A process according to claim 1, wherein a total amount of said palladium metal and rhodium metal and compound containing palladium or rhodium is about 0.0001 to about 50% by mol per mol of said aliphatic primary amine.

6. A process according to claim 1, wherein said iodine or bromine containing compound is a metal iodide or bromide.

7. A process according to claim 6, wherein said metal iodide or bromide is an alkali or alkaline earth iodide or alkali or alkaline earth bromide.

8. A process according to claim 1, wherein said iodine or bromine containing compound is an onium iodide or bromide, or a compound capable of forming an onium iodide or bromide in the carbonylation reaction system.

9. A process according to claim 8, wherein said onium iodide is one of ammonium iodides or phosphonium iodides.

10. A process according to claim 1, wherein said iodine or bromine containing compound is an oxo acid of iodine or bromine, or a salt thereof.

11. A process according to claim 1, wherein said iodine or bromine containing compound is a complex containing iodine or bromine ion.

12. A process according to claim 1, wherein said iodine or bromine containing compound is an organic iodide or bromide.

13. A process according to claim 1, wherein said carbonylation catalyst system is a combination of (1) palladium metal or a palladium containing compound and (2) iodine or an iodine containing compound.

14. A process according to claim 1, wherein a total amount of iodine atom and bromine atom in said carbonylation catalyst system is about 0.001 to about 10,000 mols per mol of the total amount of palladium and rhodium atom in said carbonylation catalyst system.

15. A process according to claim 1, wherein said aliphatic primary amine is an aliphatic primary diamine.

16. A process according to claim 15, wherein said aliphatic primary diamine is hexamethylenediamine and said aliphatic isocyanate is hexamethylene diisocyanate.

17. A process according to claim 16, wherein said aromatic hydroxyl compound is phenol.

* * * * *